(12) United States Patent
Patel

(10) Patent No.: US 8,618,348 B2
(45) Date of Patent: Dec. 31, 2013

(54) DRESSINGS WITH A FOAMED ADHESIVE LAYER

(75) Inventor: Bharat D. Patel, Princeton, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 90 days.

(21) Appl. No.: 13/246,921

(22) Filed: Sep. 28, 2011

(65) Prior Publication Data

US 2013/0079696 A1    Mar. 28, 2013

(51) Int. Cl.
*A61F 13/00*    (2006.01)

(52) U.S. Cl.
USPC .................................. 602/41; 602/42; 602/59

(58) Field of Classification Search
USPC .................................. 602/41–54; 604/385.01
See application file for complete search history.

(56) References Cited

U.S. PATENT DOCUMENTS

| | | | |
|---|---|---|---|
| 4,059,714 A | 11/1977 | Scholl et al. | |
| 4,405,063 A | 9/1983 | Wydro et al. | |
| 4,632,314 A | 12/1986 | Smith et al. | |
| 5,342,858 A | 8/1994 | Litchholt et al. | |
| 6,180,544 B1 | 1/2001 | Jauchen et al. | |
| 6,326,524 B1 | 12/2001 | Fattman et al. | |
| 6,383,630 B1 | 5/2002 | Jauchen et al. | |
| 6,586,483 B2* | 7/2003 | Kolb et al. | ................ 521/91 |
| 7,083,849 B1 | 8/2006 | Albrecht et al. | |
| 7,846,281 B2 | 12/2010 | Muvundamina | |
| 2007/0078197 A1 | 4/2007 | Samuelsen | |
| 2009/0181250 A1 | 7/2009 | Zmarsly et al. | |
| 2011/0077608 A1* | 3/2011 | Macedo, Jr. | ............ 604/385.01 |
| 2011/0196329 A1 | 8/2011 | Eckstein et al. | |
| 2012/0029105 A1 | 2/2012 | Czerwonatis et al. | |

FOREIGN PATENT DOCUMENTS

| | | |
|---|---|---|
| DE | 19620107 A | 11/1997 |
| DE | 10305224 A | 8/2004 |
| DE | 102009015233 A | 10/2010 |
| EP | 1008637 | 6/2000 |
| EP | 1315772 | 6/2003 |
| EP | 1417255 | 5/2004 |
| EP | 1986705 | 11/2008 |
| EP | 2179749 A | 4/2010 |
| JP | 2007119584 | 5/2007 |
| WO | WO 02/20687 | 3/2002 |
| WO | WO 03/011954 | 2/2003 |
| WO | WO 2004/069424 A | 8/2004 |
| WO | WO 2007/093186 | 8/2007 |
| WO | WO 2009/131920 | 10/2009 |

* cited by examiner

*Primary Examiner* — Michael A. Brown

(57) ABSTRACT

A dressing suitable for topical application to the body, including a carrier substrate having a first side and opposing second side; and a layer of a foamed adhesive composition applied to the second side of the carrier substrate, where the layer of foamed adhesive composition includes a substantially homogeneous distribution of closed cells having an inert gas contained therein.

25 Claims, 1 Drawing Sheet

Fig. 1
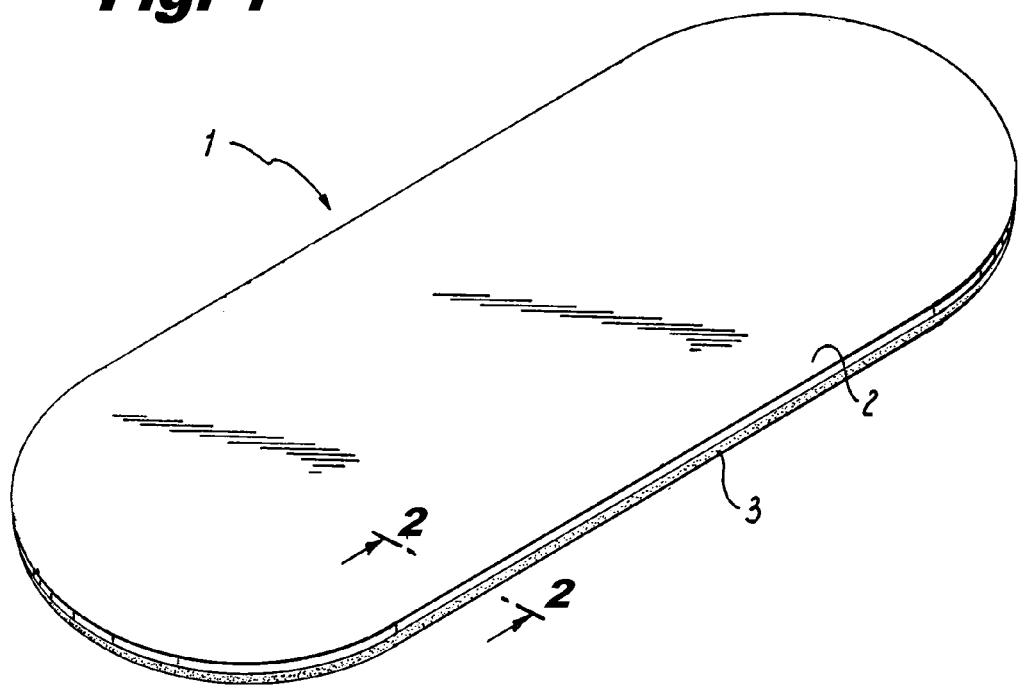
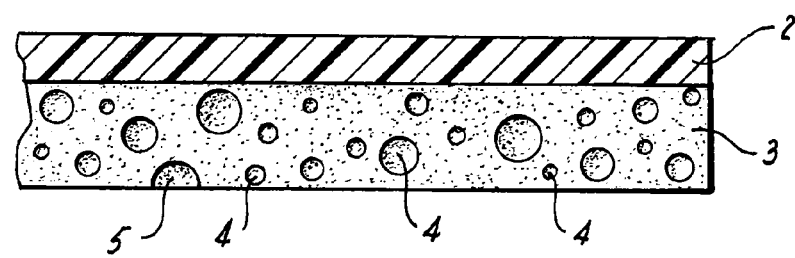
Fig. 2

DRESSINGS WITH A FOAMED ADHESIVE LAYER

FIELD OF THE INVENTION

This invention relates to a dressing for topical application to the body and that includes a carrier substrate and foamed adhesive layer applied to the carrier substrate, where the foamed adhesive layer includes a plurality of closed cells that include an inert gas disposed therein and which are substantially homogeneously distributed throughout the foamed adhesive layer.

BACKGROUND OF THE INVENTION

Adhesives for dressings that may be placed in contact with skin, either directly or indirectly, are known in the art. Such dressings include adhesive bandages for direct application to wounds in the skin, as well as absorbent articles, such as sanitary napkins, that are indirectly placed in contact with the skin via attachment to undergarments or articles of clothing. Such adhesives include hot melt adhesives.

Hot melt adhesives are applied to carrier substrates in molten form and typically will form a solid layer on the substrate upon cooling. Such adhesive compositions and layers typically will be substantially void of bubbles or pores that may contain air or other gases. Other hot melt adhesives, such as those described in U.S. Pat. No. 6,383,630, may include open cells or pores, and form open-celled adhesive layers which are said to exhibit good permeability to air and water vapor. As described therein, the adhesive composition is "applied not to the entire area of at least one side" of the carrier substrate. The adhesive layer preferably is preferably patterned in a dome form. The adhesive layers in dressings exemplified therein are applied to the carrier substrate by thermal screen printing.

Dressings of the present invention permit reduction of the amount of adhesive composition that must be applied to the carrier substrate, thus resulting in cost savings versus dressings that use a substantially similar non-foamed adhesive composition, while maintaining adhesion and bulk properties necessary for use in such dressings.

SUMMARY OF THE INVENTION

The invention relates to a dressing suitable for topical application to the body, the dressing including a carrier substrate having a first side and an opposing second side; and a layer of a foamed adhesive composition applied to the second side of the carrier substrate. The layer of foamed adhesive composition comprises a substantially homogeneous distribution of closed cells comprising an inert gas contained therein.

BRIEF DESCRIPTION OF THE DRAWINGS

The present invention will now be described in greater detail with reference to the embodiment represented in the drawings.

FIG. 1 is a perspective view of a dressing suitable for topical application to the body 1 (as further described below), showing a carrier substrate 2 (as further described below) and a layer of a foamed adhesive composition 3 (as further described below); and FIG. 2 is a cross-sectional view of the dressing illustrated in FIG. 1 taken along line 2-2 showing, in the layer of a foamed adhesive composition 3, closed cells 4 and open cells 5 (as, in each case, further described below).

DETAILED DESCRIPTION

The invention relates to dressings that are topically applied to or otherwise placed in contact with the body for use in various applications. Dressings according to the invention include, without limitation, adhesive bandages for use in wound care, e.g. for application to cuts and scrapes in the skin, and feminine sanitary protection products, e.g. napkins and liners. Such dressings will include a carrier substrate having at least one side to which a foamed adhesive composition as described herein is applied to form an adhesive layer for the purpose of securing the dressing in place relative to the body. The adhesive layer will contain a proportion of inert gas contained in a plurality of closed cells, which cells are substantially homogenously distributed throughout the adhesive layer.

Foamed adhesive compositions which can be employed in dressings of the present invention may be hot-melt adhesives having a plurality of closed cells that contain an inert gas disposed therein and which are substantially homogenously dispersed throughout the adhesive. By "substantially homogenously dispersed", it is meant that the number and volume of closed cells dispersed in any portion, e.g. volume, of the foamed adhesive composition or foamed adhesive layer is approximately the same. By "closed cell", it is meant that the cells are predominantly isolated from one another and are bounded by a definite/intact cell boundary of continuous adhesive material, i.e. a substantially continuous cell wall, such that the inert gas is encapsulated and retained within the cells.

The closed cells in the foamed adhesive composition may have an ovoid, spherical or circular structure. The closed cell in the foamed adhesive typically will have a maximum cell dimension, e.g. maximum average cell diameter, of about 10 micron, or about 5 micron. The cell dimension may range from about 1 to about 10 micron, or from about 2 to about 5 micron, depending on the particular application. While it is possible for the foamed adhesive compositions to include some relatively minor level of open cells, the cell volume in the adhesive composition is predominately made up of closed cells. Typically, the total number of cells in the adhesive composition and/or the adhesive layer will contain less than 10% of open cells, and will comprise about 90% or more of closed cells, and even more typically will comprise about 95% or more of closed cells.

The cell boundary prevents the free flow of inert gas from the closed cell in the foamed adhesive, allowing only minimal permeation. Furthermore, due to the closed cell structure, the inert gas will not easily escape from the closed cells upon application of pressure associated with applying the dressing to the carrier substrate.

In addition, the closed-cell nature of the foamed adhesive provides for a highly effective air barrier, low moisture vapor permeability and excellent resistance to water.

The foamed adhesive compositions used in the present invention may be based on materials that are used to prepare adhesives used in conventional dressings, including without limitation, natural and/or synthetic rubbers and/or on other synthetic polymers, such as acrylates, methacrylates, polyurethanes, polyolefins, polyvinyl derivatives, polyesters or silicones, or blends thereof. The adhesive compositions may also include appropriate additives, such as adhesion resins, plasticizers, stabilizers and other auxiliary components where necessary or desired.

Gases used to prepare adhesive compositions utilized in the present invention may be inert gases selected from the group consisting of nitrogen, carbon dioxide, noble gases, hydrocarbons; and air. In the case of air, anti-oxidants may be added to the adhesives. Because of the inert nature of the gases, there are no reactions between the adhesive compositions and the gases in the foamed adhesives.

For a foamed adhesive to maintain bulk adhesive properties that are effective for use of dressings of the present invention in the intended applications, and to maintain sufficient adhesive properties, the foamed adhesive needs to be prepared with the appropriate degree of foaming. The degree of foaming, i.e. the proportion of gas, e.g. volume, dispersed in and distributed throughout the adhesive composition is effective to provide the adhesive layer the requisite adhesive properties. The degree of foaming in foamed adhesive compositions used in dressings according to the present invention may be from about 15% to 70%, by volume, or from about 20% to about 60% by volume, or about 20% to 40% by volume. The density of foamed adhesive compositions used in dressings of the present invention may range from about 0.14 to 0.80 g/cm$^3$, or from about 0.19 to about 0.55 g/cm$^3$, or from about 0.19 to about 0.38 g/cm$^3$.

The foamed adhesives are prepared at the temperature just above the softening points of the adhesive material. The temperature may range from about 275° F. to about 375° F., or from about 300° F. to about 315° F. Typically, the processing temperature of the foamed adhesives to be used in dressings for use in wound care ranges from about 325° F. to about 350° F., and the temperature is slightly lower for foamed adhesives to be used in dressings for use in sanitary protection. The mixing is conducted at a relatively high speed. In addition to temperature and speed of mixing, other conditions of preparing the closed-cell foamed adhesive compositions must be effective to provide the closed-cell structures substantially homogeneously dispersed therein.

In order to prepare foamed adhesives with predominately closed cells, as described above, a particularly suitable process for producing the foamed adhesives is employed as described herein. In this process, the pressure sensitive adhesive is first melted at a temperature greater than the melting point of the adhesive, then mixed with dry inert gases, such as nitrogen, air or carbon dioxide, in different proportions by volume, e.g. 10-80%, under high pressures in sequential mixers, each equipped with single blade. Such sequential mixers are composed of two mixers, the coarse mixer and the fine mixer, which enables the production of the closed cells. The gases e.g. $N_2$, are pumped into the molten adhesive at high pressure, e.g. from about 800 to about 1500 psi, such that the adhesive pressure is approximately 40-100 psi in the first mixer, where the coarse mixing occurs. Then the pre-mixture of gases and molten adhesive is subsequently pumped into the second mixer in order to continue fine mixing to yield the foamed adhesives with a substantially homogeneous distribution of closed cells. Additional gas optionally may be added to the second mixer. Additional mixers may be used as required. The external pressure, i.e. the die pressure, is maintained at 300-600 psi. The mixing speed varies from equipment to equipment, but it must be sufficiently high to yield a substantially homogeneous distribution of the closed cells containing the gas in the adhesives. An exemplary mixing speed is about 100 to about 1000 rpm. Further, to maintain the closed nature of the cell, the viscosity of the molten adhesives should be in the range of 1,000-50,000 cps, at the temperature where the mixing of the gases and molten adhesives occurs to sustain the close cells. The foamed adhesive mixture is transferred through insulated (i.e. temperature controlled) pipes to the dispensing station and dispensed through a slot die onto the carrier substrate. The slot die can be designed to dispense various patterns to the surface of the substrate, whether over the entire or partial area of the substrate.

Carrier substrates used in the invention may be any substrate conventionally used in applications in which the dressings of the invention may be used. The foamed adhesive is applied to the substrate in order to secure the dressing in place in relationship to the surface of the body to which the dressing is applied. The carrier substrates will have a first side and a second side, opposite the first side, to which the foamed adhesive composition is applied to form the foamed adhesive layer. The adhesive layer may be continuous, i.e. covering substantially the entire area of the second side of the substrate to which it is applied. The adhesive layer also may be discontinuous, in which case the foamed adhesive may be applied in a pattern, or around the periphery of the second side of the substrate, and the like, thus having adhesive areas and non-adhesive areas. The total adhesive area must be sufficient to secure the dressing in place.

In the case of adhesive bandages, the second side of the substrate having the foamed adhesive layer thereon will be placed directly on the skin, securing the bandage directly to the skin. An absorbent pad may be applied onto the surface of the adhesive layer facing the skin, in which case the adhesive layer may serve to adhere the bandage to the skin, as well as to adhere the absorbent pad to the carrier substrate, e.g. a backing layer conventionally used in adhesive bandage applications.

In the case of a sanitary napkin embodiment, the carrier substrate may be used in conjunction with other absorbent pads or layers in order to provide requisite absorption of body fluids. The second side of the carrier substrate having the foamed adhesive layer applied thereto is then place in contact with the undergarment or other article of clothing to secure the napkin in place.

The substrates may be made from woven or knitted fabrics, elastic or inelastic materials, plastic films, paper, nonwovens fabrics, foam materials, or laminates thereof. Polymeric materials that may be used in preparation of the carrier substrate include, but are not limited to, polyethylene, polyolefinic films, coextruded polyolefinic films, polyurethane film, and PU/PVC foam backing. In certain adhesive bandage embodiments, the carrier substrate may be a smooth surface or apertured film, such as mono- or co-extruded polyolefin films, e.g. polyethylene or polypropylene, polyurethane or other thin films. Other substrates include a coarse, textured surface/topography as with woven or non-woven flexible fabrics made from, e.g. natural or synthetic fibers such as cotton, rayon, PET, nylon, polyurethane, etc. In embodiments where the dressing is a sanitary napkin, the carrier substrate may be a film, e.g. polyethylene, or a non-woven e.g. polypropylene.

The foamed adhesive compositions having the closed cells distributed there through are applied to the side of the carrier substrate that secures the dressing of the present invention in relationship to the body. As noted above, the side containing the foamed adhesive layer secures the adhesive bandage to the skin, while the side containing the foamed adhesive layer secures the sanitary napkins or liner to an article of clothing.

As in the foamed adhesive composition, the closed cells distributed throughout the foamed adhesive layer have a cell dimension that may range from about 1 to about 10 micron, or from about 2 to about 5 micron. In some embodiments of the invention, the closed cell may be elongate in structure due to application of the foamed adhesive composition to the carrier substrate, in which case the cell dimension may be length and/or width of the cell. In other embodiments, the closed cell may be ovoid, spherical or circular in structure, in which case the cell dimension may be an average cell diameter. In certain embodiments the cell dimension has a maximum of about 10 micron, or in other embodiments, the cell dimension has a maximum of about 5 micron.

The thickness of the foamed adhesive layer may be from about 20 to about 200 micron, or from about 30 to about 100 micron. The ratio of the thickness of the foamed adhesive layer to the average cell dimension may be from about 0.005 to about 0.50, or from about 0.03 to about 0.1. The foamed adhesive layer may have a basis weight ranging from about 20 to about 150 g/m$^2$, or from about 30 to about 100 g/m$^2$, or from about 30 to about 60 g/m$^2$. The density of the foamed adhesive layer may be from about 0.14 to about 0.80 g/cm$^3$, or from about 0.19 to about 0.55 g/cm$^3$, or from about 0.19 to about 0.38 g/cm$^3$.

In preparation of the adhesive dressings of the present invention, the foamed adhesive composition as described herein are coated onto the side of the carrier substrate that will secure the dressing in place in relation to the body.

Adhesive dressings of the present invention exhibit a number of advantages. First, the amount of adhesive required to be used in the adhesive layer is considerably reduced by the presence of the closed cells filled with gases without adversely affecting the adhesion properties and bulk properties of the adhesive layer. This provides a significant savings to the manufacturer due to the reduced amount of adhesive composition actually used. Further, the foamed adhesive layer gives the adhesive dressing a soft and smooth feel, providing an improved comfort upon application.

The adhesive dressings typically have a static shear that is about 20% to about 80% of the static shear of an adhesive dressing comprising substantially the same, or the same, carrier substrate, and a layer of non-foamed adhesive composition that is substantially similar to the foamed adhesive composition. In certain embodiments the dressings of the invention will have a static shear of about 60%, or about 80% of the static shear of an adhesive dressing comprising substantially the same, or the same, carrier substrate, and a layer of non-foamed adhesive composition that is substantially similar to the foamed adhesive composition. The dressings may have a static shear of about 100 minutes or greater, or 300 minutes or greater, or about 500 minutes or greater, or about 1500 minutes or greater, each as determined by methods referenced and described herein below with a static load at 500 g. As set forth in the claims, all static shear values are determined by the methods described in ASTM 6463, at a static load of 500 g.

Example 1

A hot-melt adhesive composition with no foaming was applied to two different carrier substrates, one being a flexible, woven PET fabric (Control C1) and the other a polyolefin film having outer films of PE and a film of PE/acrylic blend disposed between the outer films (Control C2). Hot-melt adhesive compositions of varying degrees of foaming were applied to the same substrates as C1 and C2, respectively. The hot-melt adhesives were applied to the various carrier substrates at approximately 160° C. The resulting coated substrates, C1, C2, 1A, 1B, 1C and 1D, were then tested for 90° Adhesion and static shear utilizing standard test methods ASTM 3330 F and ASTM 6463, respectively. Results are presented below.

|  | Flexible Fabric | | | PE Backing (Sheer) | | |
| --- | --- | --- | --- | --- | --- | --- |
|  | C1 | 1A | 1B | C2 | 1C | 1D |
| Basis Weight (g/m$^2$) | 58 | 40 | 28 | 50 | 38 | 25 |
| Foaming (Volume %) | 0 | 31 | 51 |  | 24 | 50 |
| Thickness (mil) | 16.5 | 11.9 | 12.6 | 6.0 | 5.7 | 5.3 |
| 90° Adhesion/Glass (oz/in) | 19 | 17 | 14 | 20 | 10 | 4 |
| 90° Adhesion/Backing (oz/in) | 12 | 7 | 6 | 34 | 16 | 8 |
| Static Shear (min.) 0.75" × 0.75" × 500 g (Static Load) | 545 | 308 | 195 | >6000 | >6000 | >6000 |
| Static Shear (min.) 0.75" × 0.75" × 750 g (Static Load) | 156 | 98 | n/a | Backing breaks-unable to measure | | |

As the results indicate, the woven fabric having a foamed adhesive layer containing about 30 and 50% foaming (by volume) exhibited a static shear of 308 and 195 minutes at a static load of 500 g, respectively. The polyolefin films with the same adhesive layer exhibited static shear that were immeasurable.

What is claimed is:

1. A dressing suitable for topical application to the body, comprising:
   a carrier substrate having a first side and opposing second side; and
   a layer of a foamed adhesive composition applied to the second side of the carrier substrate, wherein the layer of foamed adhesive composition consists essentially of an adhesive and a substantially homogeneous distribution of closed cells comprising an inert gas contained in the adhesive, wherein the foamed adhesive composition has a soft feel for providing improved comfort.

2. The dressing of claim 1 wherein the closed cells are ovoid, spherical, circular or elongate in structure.

3. The dressing of claim 1 wherein the closed cell comprises a cell dimension selected from the group consisting of average diameter, length and width.

4. The dressing of claim 3 wherein the cell dimension is from about 1 to about 10 micron.

5. The dressing of claim 3 wherein the cell dimension is from about 2 to about 5 micron.

6. The dressing of claim 1 wherein the layer of the foamed adhesive composition has a thickness from about 20 to about 200 micron.

7. The dressing of claim 1 wherein the layer of the foamed adhesive composition has a thickness from about 30 to about 100 micron.

8. The dressing of claim 1 wherein a ratio of the thickness of the layer of the foamed adhesive composition to the cell dimension is from about 0.005 to about 0.50.

9. The dressing of claim 1, wherein a ratio of the thickness of the layer of the foamed adhesive composition to the average cell diameter is from about 0.03 to about 0.1.

10. The dressing of claim 1, wherein the foamed adhesive composition has a density from about 0.14 to about 0.80 g/cm$^3$.

11. The dressing of claim 1, wherein the foamed adhesive composition has a density from about 0.19 to about 0.55 g/cm$^3$.

12. The dressing of claim 1 wherein the Inert gas is selected from the group consisting of nitrogen, carbon dioxide, noble gases, hydrocarbons and air.

13. The dressing of claim 1 wherein the layer of foamed adhesive composition comprises from about 15% to about 70% by volume of the inert gas.

14. The dressing of claim 1 wherein the layer of foamed adhesive composition comprises from about 20% to about 60% by volume of the inert gas.

15. The dressing of claim 1 wherein the layer of foamed adhesive composition comprises from about 20% to about 40% by volume of the inert gas.

16. The dressing of claim 1 having a static shear of about 100 minutes or more.

17. The dressing of claim 1 having a static shear of about 300 minutes or more.

18. The adhesive dressing of claim 1 having a static shear of about 1500 minutes or more.

19. The dressing of claim 1 having a static shear of about 20% to about 80% of the static shear of an adhesive dressing comprising the carrier substrate and a layer of non-foamed adhesive composition, wherein the non-foamed adhesive composition is substantially similar to the foamed adhesive composition.

20. The dressing of claim 1 having a static shear of about 60% to about 80% of the static shear of an adhesive dressing comprising the carrier substrate and a layer of non-foamed adhesive composition, wherein the non-foamed adhesive composition is substantially similar to the foamed adhesive composition.

21. The dressing of claim 1 wherein the adhesive layer has a basis weight of from about 20 to about 150 g/m2.

22. The dressing of claim 1 wherein the adhesive layer has a basis weight of from about 30 to about 100 g/m2.

23. The dressing of claim 1 wherein the adhesive layer has a basis weight of from about 30 to about 60 g/m2.

24. The dressing of claim 1 wherein the closed cells comprise about 90% or more of the total number of cells in the adhesive layer.

25. The dressing of claim 1 wherein the closed cells comprise about 95% or more of the total number of cells in the adhesive layer.

* * * * *